(12) United States Patent
Valsesia et al.

(10) Patent No.: US 8,508,744 B2
(45) Date of Patent: Aug. 13, 2013

(54) SURFACE PLASMON RESONANCE SENSING METHOD AND SENSING SYSTEM

(75) Inventors: Andrea Valsesia, Ranco (IT); Pascal Colpo, Angera (IT); Francois Rossi, Cittiglio (IT); Franco Marabelli, Pavia (IT)

(73) Assignees: The European Union, Represented by the European Commission (BE); University of Pavia (IT)

( * ) Notice: Subject to any disclaimer, the term of this patent is extended or adjusted under 35 U.S.C. 154(b) by 0 days.

(21) Appl. No.: 13/379,073

(22) PCT Filed: Jun. 18, 2010

(86) PCT No.: PCT/EP2010/058647
§ 371 (c)(1),
(2), (4) Date: Feb. 2, 2012

(87) PCT Pub. No.: WO2010/146160
PCT Pub. Date: Dec. 23, 2010

(65) Prior Publication Data
US 2012/0120401 A1    May 17, 2012

(30) Foreign Application Priority Data
Jun. 19, 2009   (EP) .................................. 09163292

(51) Int. Cl.
*G01N 21/55* (2006.01)
(52) U.S. Cl.
USPC ......................................... 356/445; 356/448

(58) Field of Classification Search
USPC ...... 356/445–448, 128, 135, 136; 422/82.05, 422/82.09; 436/164, 165, 171–172
See application file for complete search history.

(56) References Cited

U.S. PATENT DOCUMENTS

| | | | |
|---|---|---|---|
| 7,754,153 B2 * | 7/2010 | Miyamoto et al. | 422/82.09 |
| 2008/0316490 A1 | 12/2008 | Yen | |
| 2009/0021727 A1 | 1/2009 | Sepulveda Martinez et al. | |
| 2011/0157593 A1 * | 6/2011 | Miyadera et al. | 356/445 |

FOREIGN PATENT DOCUMENTS

| | | |
|---|---|---|
| EP | 1729110 A2 | 6/2006 |
| EP | 1906171 A2 | 4/2008 |
| GB | 2197065 A | 5/1998 |

OTHER PUBLICATIONS

International Search Report PCT/EP2010/058647: Dated Sep. 27, 2010.

(Continued)

*Primary Examiner* — Tri T Ton
(74) *Attorney, Agent, or Firm* — Cantor Colburn LLP

(57) ABSTRACT

A SPR sensing method comprising the steps of: providing a SPR sensor comprising a SPR supporting sensor surface and contacting a sample to be analysed with the sensor surface. At least one resonance condition at said SPR supporting sensor surface is monitored by illuminating the sensor surface with an SPR exciting test light beam and sensing the reflected or transmitted test light beam. Additionally, the sensor surface is illuminated with a reference light beam under conditions selected so as not to excite SPR at said sensor surface and sensing the intensity of the reflected or transmitted reference light beam. At least one property of the reflected or transmitted test light beam is determined taking into account the sensed intensity of the reflected or transmitted reference light beam.

19 Claims, 3 Drawing Sheets

(56) References Cited

OTHER PUBLICATIONS

Homola J., "Dual-channel surface Plasmon resonance sensor with spectral discrimination of sensing channels using dielectric overlayer", Electronic Letters, Jun. 24, 1999, vol. 35, No. 13 XP 002568586.

Homola J., "Present and fugure of surface Plasmon resonance biosensors", Anal Bioanal Chem (2003) 377: 528-539, XP 002568587.

Niamushin A.N, "A portable surface Plasmon resonance (SPR) Sensor system with temperature regulation", Sensors and Actuators B 96 (2003) 253-260, XP002568588.

* cited by examiner

SURFACE PLASMON RESONANCE SENSING METHOD AND SENSING SYSTEM

TECHNICAL FIELD

The present invention generally relates to a surface plasmon resonance (SPR) sensing method and to a SPR sensing system. The invention more particularly relates to a SPR sensing method and to a SPR sensing system suitable for use i.a. in chemical, biochemical, biological, biomedical, pharmaceutical and physical testing.

BRIEF DESCRIPTION OF RELATED ART

There are many known sensors using the excitation of surface plasmons, termed Surface Plasmon Resonance (SPR) Sensors, for detecting refractive index changes in a sample adjacent to a sensor surface. Such SPR sensors are used e.g. for quantifying concentrations of substances in chemical, biochemical, biological, biomedical or pharmaceutical research, in clinical or food diagnosis or in environmental measurements (e.g. detection of gas or wastewater), etc. Many SPR sensors can perform fast, parallel and massive inspections, which make these sensors also convenient for quantifying molecular interactions, in particular for studying the affinity and the real-time reaction kinetics between two or more interacting molecules.

SPR sensors rely on the well-known SPR phenomenon, which involves one or more surface-bond electromagnetic waves that propagate at an interface between a metallic material (typically gold or silver) and a dielectric material. Each surface-bond electromagnetic wave, which is due to a collective oscillation of free electrons at the metal-dielectric interface, propagates with its highest intensity parallel to this interface and decays exponentially away from this interface.

Conventionally, a SPR sensor comprises a sensor surface supporting surface plasmons, where SPR can be optically excited. It is well known that light can excite the resonance of surface plasmons at a metal-dielectric interface if an interface-parallel component of the incident light and a surface-bond electromagnetic wave of the SPR both have matching frequencies and matching wavelengths. In the resonance condition, the incident light is absorbed by the metal-dielectric interface so as to couple with the surface-bond electromagnetic wave. It is then possible to observe this absorption by detecting for example a reduction in the intensity of the light that is transmitted or reflected by the metal-dielectric interface. The coupling condition between light and surface plasmon waves being very sensitive to refractive index changes of the dielectric medium close to the metal-dielectric interface, SPR sensors take advantage of this sensitivity in the resonance coupling condition for detecting changes in the refractive index of a dielectric medium by measuring the decrease in intensity of light reflected from the metal-dielectric interface, while the latter is illuminated with an SPR exciting light beam.

SPR finds particular application in biosensor systems capable of detecting interactions between biomolecules or biochemical molecules, for example interactions between antigens and antibodies, enzymes and ground substances, endocrines and receptors, nucleic acids and nucleic acids, etc. In particular, many SPR biosensor systems have receptors or ligands attached on their sensor surface so as to detect changes in the light-SPR coupling condition caused by refractive index changes at the sensor surface when biochemical molecules or biomolecules interact with (bind to) these receptors or ligands. Such biosensor systems are suitable for measuring for example concentrations of biomolecules or biochemical molecules in solutions, etc.

Currently, there is a variety of laboratory equipments that are based on such SPR sensing. US patent application No. 2009/021,727, e.g., describes a SPR sensing method and device for detecting refractive index changes of a dielectric medium, in particular for detecting biomolecules. According to the sensing method described in this document, a transversal magnetic polarized light is directed towards a magnetized metallic layer so as to excite SPR on this metallic layer, wherein the light is at least partly reflected by the metallic layer towards a detector. The detector then detects a feature of the reflected light and produces a signal that is thereafter analyzed for determining an absolute value of a refractive index, a magnitude and/or an indication of occurrence of a change in refractive index of a dielectric medium adjacent to the metallic layer.

Another SPR biosensor system for detecting biochemical molecules is known from US° 2008/316,490. This system comprises a sensor featuring a metallic detection film arranged on a glass substrate, where the metallic detection film is covered by a metallic grating structure. The metallic material used for this sensor comprises gold, silver or copper. Micelles are deposited on the sensor surface formed by the detection film and the grating structure so as to enable reaction with biomolecules. A liquid sample containing biomolecules is then disposed on this surface, whereby analyte biomolecules will react with these micelles and thereby induce a change in the refractive index at the sensor surface. This change in refractive index is detected by illuminating the sensor surface so as to excite SPR thereon and by detecting an intensity change of the reflected light.

EP 1729110 discloses an optical biosensor having noble metal nanoparticles. Light is irradiated from a light source to the noble metal nanoparticles through an optical fiber and reflected light is introduced to one or more optical detecting units through another optical fiber. The optical detecting unit separately measure the intensity of the input light in a main band including a maximum absorption wavelength, as well as in a couple of auxiliary bands that have respectively have longer and shorter wavelength. The auxiliary bands are in spectral proximity of the main band and are used to evaluate the amount of the shift of the resonant wavelength of the noble metal nanoparticles due to the change of the refractive index.

The above-mentioned SPR sensing systems are however subject to multiple detection and/or measurement errors of the properties that are of interest, such as refractive indexes or refractive index changes, etc. Such errors can may be caused by external effects such as e.g. temperature variations of a sensor surface and/or of an examined medium, changes or fluctuations in a measured light intensity and/or in a measured polarization of a light beam along its optical path, instabilities of light sources, noise signals interfering with a sensed signal, mechanical shocks on the sensor, etc. It is interesting to note that such extraneous effects can cause undesired changes in the intensity or polarization of a light beam to be detected or measured, which are frequently referred to as artefacts. Moreover, the above-mentioned SPR based sensing systems are not adapted to detect if an artefact has occurred, nor are they adapted to correct such artefacts.

BRIEF SUMMARY

Hence, there is a need for a SPR sensing method or SPR sensing system that is able to detect and/or take into account the occurrence of such artefacts for an improved reliability.

In order to be able to detect the occurrence artefacts during SPR sensing, the present invention proposes, in addition to monitoring the surface plasmon resonance condition related to the sample under investigation, to also monitor the reflected or transmitted intensity of a reference light that does not excite SPR.

Indeed, monitoring reflected or transmitted light intensity under non-SPR conditions can advantageously be used to check fluctuations or drifts that are not affected by the phenomenon of interest, i.e. the shift in SPR due to variations in refractive index at the sensor surface. The present inventors have in fact observed that fluctuations of such transmitted or reflected reference light is caused by extraneous phenomenons, e.g. temperature variations or instabilities of the light source.

According to the present method, a resonance condition is monitored by illuminating the sensor surface with at least one test light beam so as to excite SPR, and the reflected or transmitted test light is sensed and preferably measured. It will be understood that, in order to excite SPR at the sensor surface, the at least one test light beam has one or more frequencies that match to one or more frequencies of surface-bond electromagnetic waves at the sensor surface. Simultaneously or alternatively, the sensor surface is illuminated by at least one reference light beam under conditions selected so as not to excite surface plasmon resonance at said sensor surface, and the reflected or transmitted intensity is measured. According to an important aspect of the invention, the sensed or measured reflected or transmitted intensity of the reference light beam is taken into account in the determination of a light property, e.g. the intensity, of the at least one test light beam as transmitted or as reflected by the sensor surface.

Taking into account the measured intensity of the reflected/transmitted reference light while performing SPR permits determining the occurrence of an artefact and even more interestingly a systematic correction of the measured test values. Accordingly, sensed reference light beam can be as a basis for filtering or correcting the sensed/measured test light beam.

Preferably, the reference light beam covers a spectral band the spectral limits of which are at a spectral position far at least the double of the Full Width at Half Maximum of the Surface Plasmon Resonance from the (closest) Surface Plasmon Resonance peak (considering the centre of the peak). Such reference light beam (respectively the corresponding monitored band) preferably has a narrow spectral width, e.g. in the order of 100 nm or less.

The present invention can be implemented based on any kind of SPR sensing technology, e.g. relying on the conventional Kretschmann approach or on the more recent use of periodic metallic nanogratings as surface sensing layer, or other suitable surface sensing layer configuration supporting localized and/or delocalized SPR, inasmuch the selected technology allows monitoring the reflectivity/transmittivity of a non-SPR motivating reference light beam at the sensor surface.

It may be noted that since resonance conditions are essentially determined by the sensor design, illumination under SPR exciting or non-exciting conditions is determined by appropriate selection of incidence angle and wavelength (respectively wave number). It is sufficient to appropriately vary one of the incidence angle and wavelength to switch from a resonance motivating illumination condition to a non-resonance motivating illumination. Nevertheless, one could vary both.

The monitoring for the reference signal can be performed at any appropriate time. Ideally, a reference light measurement is carried out for each test measurement, either simultaneously or in alternating manner. In the latter case, test and reference measurement should preferably be very short (in the order of one or a few milliseconds each, separated by a very short switching period—also milliseconds).

Preferably, the present method involves measuring one or more spectral intensities, i.e. intensities that correspond to specific frequencies, and/or determining changes in one or more spectral intensities of at least one test light beam or of at least one reference light beam as transmitted or as reflected by the sensor surface. More preferably, the method involves determining a maximum change of the measured spectral intensities so as to detect an occurrence of SPR excitation at the sensor surface. Preferably, the present method proposes determining a maximum change of the measured spectral intensities for determining a value indicative of the extent of a change in the light-SPR coupling condition at the sensor surface.

The measured light property of at least one test light beam may be a measured intensity, in particular a measured time- or frequency-weighted average intensity, or a measured change in intensity, in particular a measured change in a time- or frequency-weighted average intensity, of the at least one test light beam. It may be noted that a change in a measured time- and/or frequency-averaged intensity of at least one test light beam can be indicative of a measured time- and/or frequency-averaged intensity change or of a measured change of a time- and/or frequency-averaged intensity and vice versa. Besides, a measured light property can also be indicative of a polarization of the at least one test light beam as transmitted or as reflected by the sensor surface.

It may be further noted that a time- or frequency-weighted average intensity of a reference light beam and/or of a test light beam can be indicative of a time-weighted average intensity and/or of a frequency-weighted average intensity. A monitored or a measured time-weighted averaged intensity is preferably indicative of a monitored or of a measured intensity averaged over one or more time intervals, preferably in the range of milliseconds. However, a monitored or a measured frequency-weighted average intensity of a light beam may be indicative of an average spectral intensity, i.e. of a mean value of spectral intensities, which is weighted by the frequencies that compose the spectrum of the light beam. In particular, when a reference or a test light beam presents a continuous spectral band, a measured frequency-weighted average intensity can be indicative of an integration, in particular of a numerical integration, of the measured intensities over the spectrum of the light beam.

The monitored intensity of the reference light beam and/or a measured intensity of the test light beam can be indicative of a measured reflectivity, reflectance, transmittivity, transmittance, absorbance etc. of the corresponding light beam.

In one embodiment, the present method proposes processing, in particular filtering, a measured light property of at least one test light beam or a measurement thereof by using a determined drift value indicative of a deviation of the monitored intensity of the reference light beam as transmitted or as reflected by the sensor surface, in order to exclude or validate a measured test value. Various known approaches are available for performing such filtering. One possibility is to exclude measured test values when the corresponding drift value exceeds a predetermined threshold. Alternatively, one may consider that if a measured intensity test value is at least three times the noise value (i.e. the reference intensity value), then the measured intensity test value is considered correct.

In another embodiment, a drift value can be used for correcting a measured intensity of reflected/transmitted test beam, in particular a measured time- or frequency-weighted average intensity, or a change in a measured intensity, in particular a change in a measured time- or frequency-weighted average intensity, of the at least one test light beam. For example, a measured intensity of a test light beam can be corrected by performing calculations, such as linear combinations, in particular subtractions, between this measured intensity or this measured time- or frequency-weighted average intensity and the drift value.

As it is known to those skilled in the art, in classical SPR methods, the resonance mode is only de-localized and exists for a set of given combinations between the angle of incidence and the wavelength. Accordingly, illuminating said sensor surface with a reference light beam under conditions selected so as not to excite SPR may be carried out by operating at an angle that does not excite SPR, i.e. operating at an angular distance far enough from the resonance angle.

Modern SPR employs nanogratings where de-localized modes and localize modes exist. The de-localized modes behave in the same way than the above described case, whereby at fixed wavelength, one can find some "angular intervals" where the SPR is not excited. The localized modes however are dispersionless, meaning that they exist at a fixed wavelength for all the angles. Accordingly, when operating with nanogratings based SPR sensors, one shall typically switch from SPR exciting or non-exciting conditions by varying the wavelength. From the practical point of view it is also much easier as it avoids any displacements of light beams.

According to another aspect of the present invention, there is proposed a SPR sensing system, which is suitable for performing the method.

Preferably, the photosensor is adapted to measure an intensity, in particular a time- or frequency-weighted average intensity, or a change in intensity, in particular a change in a time- or frequency-weighted average intensity, of at least one test light beam as transmitted or as reflected by the sensor surface. More particularly, the photosensor may be adapted to monitor an intensity, preferably a time- or frequency-weighted average intensity of the at least one reference light beam as reflected or as transmitted by the sensor surface, and configured to use a drift value to correct the measured intensity, the measured time- or frequency-weighted average intensity or a change thereof.

Preferably, the sensor surface comprises a sensing layer designed as a periodic metallic nanograting, the metal being e.g. gold, silver or other noble metals used in the art. The sensor surface is advantageously supported on a transparent substrate capable of transmitting the test and reference light beams, which permits detection in reflection mode. The substrate may be made from glass or light-transparent polymer.

For biosensing applications, targeting moieties exhibit binding specificity to desired analytes may typically be attached on the sensor surface. The targeting moieties are preferably organised as a microarray and may be of different kinds. The targeting moities may be attached to the sensor surface through an appropriate hydrogel layer, e.g. a PEG layer.

In one preferred embodiment, the sensing system comprises a sensor with a sensor surface with a periodic gold nanograting and a mircroarray of targeting moieties attached thereon. The system is configured for operating in reflection mode and comprises a CCD detector as well as one LED for emitting the reference light beam and at least one led, preferably two, for monitoring the respective resonance coupling positions. This is a particularly advantageous embodiment that can be build as a pocket size SPR apparatus enabling the measurement in multiplexed mode of various biochemical species with high reliability and accuracy, without risks of measurements errors due to artefacts.

These and other preferred embodiments of the present method and system are recited in the dependent claims.

BRIEF DESCRIPTION OF THE DRAWINGS

Further details and advantages of the present invention will be apparent from the following detailed description of several not limiting embodiments with reference to the attached drawings in which.

DETAILED DESCRIPTION

Figure 1:
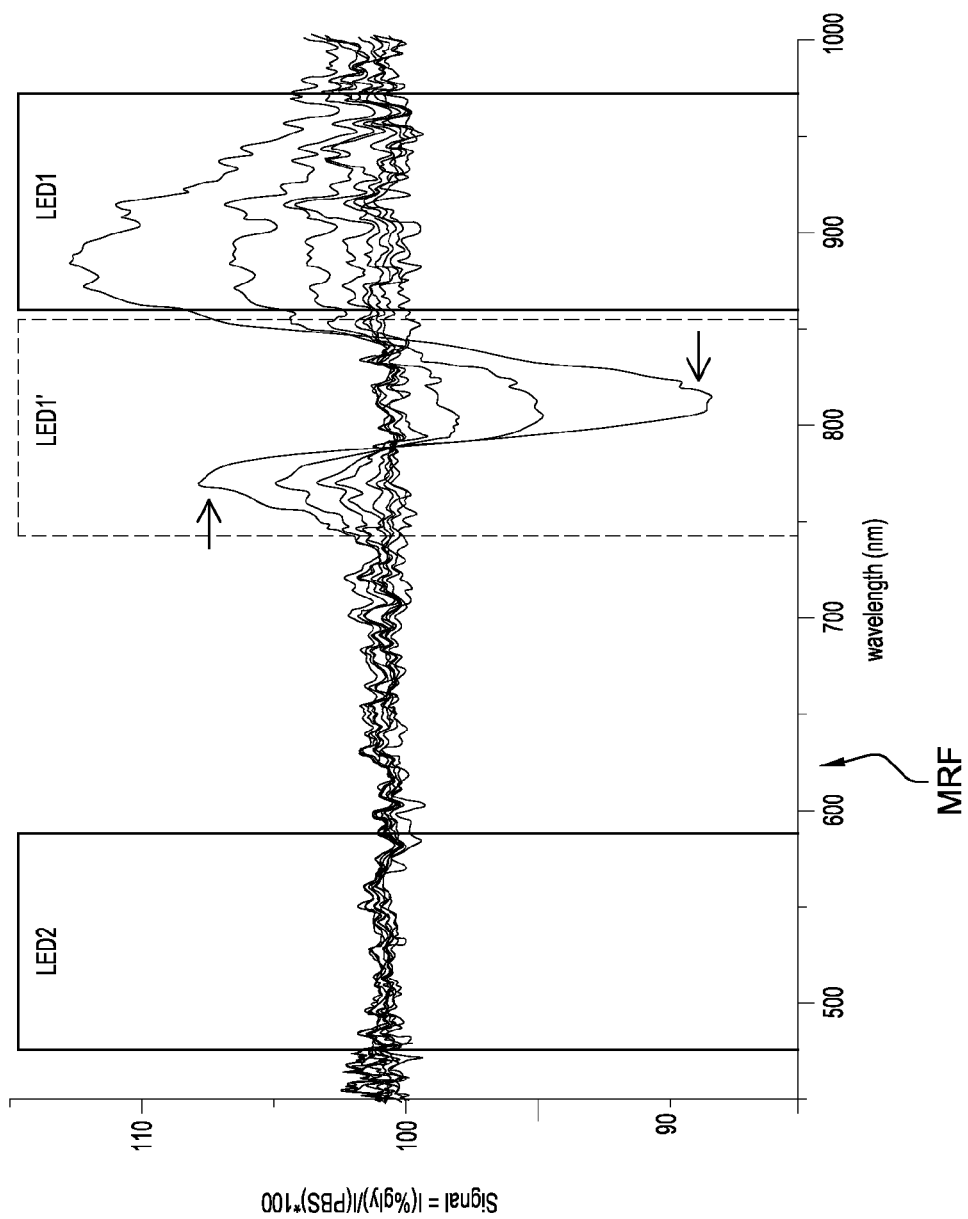
FIG. 1: is a graph showing a set of frequency-resolved curves indicative of intensities of a test light beam and of a reference light beam that have been measured for different values of refractive index of a medium in contact with the sensor surface.

The present invention provides a reliable method of SPR sensing, which takes into account the occurrence of artefacts, i.e. events that are extraneous to the phenomenon under observation and that affect the accuracy of the measurements.

As it is well known, conventional SPR analysis methods are based on changes in the optical reflectivity of a thin metal film (typically Gold) when contacted with a liquid (or possibly gaseous) sample of interest. Typically, such method involves exciting the surface plasmons at the metal/sample interface by means of a test light beam and detecting the reflected (or transmitted) light, the intensity of the reflected light depending on the coupling of the incident test light beam and to the propagating surface plasmon waves.

On a resonance condition, i.e. where a resonance coupling is obtained between the incident test light and the surface plasmon waves, a strong attenuation in intensity of the reflected test light is observed. This resonance condition is very sensitive to the index of refraction of the sample and is traditionally tracked by varying the illumination conditions. In typical laboratory setups, the resonance is monitored by following the variation of light intensity versus wavelength or incident angle. In other, more practical SPR systems, the shift of the resonance condition is tracked by following the variation of the reflected intensity under a punctual incident light beam generated e.g. by a LED with narrow bandwidth or laser.

The present method relies on the SPR technique and provides for a way of taking into account artefacts occurring during measurements. This is achieved by monitoring the reflectance (transmittance) of the SPR supporting sensor surface under conditions that do not excite the resonance so as to detect a drift or change in the reflected intensity (resulting from an incident reference light beam) that is not due to resonance coupling between the incident light beam and the surface plasmon waves. Hence, the inventive method uses an optical property of the surface which is purposely not related to any plasmon resonance supported by the surface.

Such detection of artefact is applicable with any SPR sensing technique, where a reflected or transmitted signal intensity can be measured under illumination conditions selected so as not to excite SPR.

The following description of the present method and system with reference to the Figs. is directed to a preferred embodiment with a preferred sensor structure having a sensor surface supporting localized and de-localized SPR and adapted for biosensing as well as to a sensing system configured for operation in reflection mode and at fixed angle of incidence.

The present method as applied to such biosensor can be implemented as follows. A sample to be analysed is contacted with the surface of a sensor suitable for supporting SPR. A preferred embodiment of such a sensor will be described in more detail below with reference to FIGS. 4 and 5, however it may be noted that it preferably has a sensor surface comprising a periodic metallic nanograting of a noble metal (here gold) in order to support localized and delocalized SPR. The geometrical and physical properties of this nanograting determine the optical response of the sensor.

Upon contacting the sensor surface with a sample to be analysed, the sensor surface is illuminated by a test light beam having a frequency and incident angle known to be able to excite SPR at the sensor surface. It may be noted that the test light beam illuminating the sensor surface can be configured in a manner known per se to have a given polarization. In order to excite SPR, the test light beam has one or more frequencies that match with one or more permitted frequencies of the surface-bond electromagnetic waves at the sensor surface. Preferably, the sensor is designed so that the permitted frequencies of SPR correspond typically to the visible/near-infrared spectrum of light. As the test light beam excites SPR, at least part of the test light beam is absorbed at the sensor surface, where the extent of absorption depends on the frequency of the incident light at the sensor surface. The light of the test light beam that has not been absorbed at the sensor surface is then reflected or transmitted by the sensor surface.

Then a light property of the reflected test light beam, preferably its intensity, is sensed (measured) and an actual value of the measured light property is determined, which is representative of the level of excitation of the surface plasmons and allows assessing a state of resonance or the shift of the resonance condition established with respect to calibrated or previously stored/acquired data. As it is known, a resonance condition typically leads to a decrease in the measured intensity of the reflected light of the test light beam due to the absorption of the light at the sensor surface, and a modification in the refractive index of the sample adjacent to the sensor surface causes a shift of the resonance condition.

During such measurement of reflected intensity of a test light, the measurement may be affected by extraneous, spurious effects such as temperature or light source fluctuations, variations in the sensitivity of the detector or modifications in the mechanical configuration, which alter the overall response of the sensing system. Such artefacts thus cause a deviation or drift of the measured intensity of the reflected test light, as compared to the measured value that would have been obtained without any artefact and are thus erroneously interpreted as a change in refractive index.

It will be appreciated that, to be able to check the occurrence of such artefact and/or to correct the determined intensity value, it is proposed to illuminate the sensor surface by a reference light beam under conditions that are selected so as not to excite SPR at the sensor surface. Accordingly, the reference light beam has one or more frequencies that do not match to any permitted frequency of surface-bond electromagnetic waves at the sensor surface (the angle of incidence being fixed in this variant). In other words, the reference light beam has one or more frequencies that are not in a spectral band causing a resonance condition at the sensor surface. Monitoring the intensity of the specularly reflected reference light (i.e. of the reflected beams having spectral wavelengths/bands that do not excite SPR—thus at an appropriate spectral distance from the resonance) over time allows determining a variation in the intensity of the reflected reference light that is not due to SPR, and thus indicates a change in the sensor system that is not due to the phenomenon under observation.

As it will be explained in more detail below, the reference light beam can be exploited simply to detect a drift of the measurement due to an artefact (hence for filtering purposes), but can also be taken into account for correcting the reflected test light intensity values, providing a kind of noise correction.

Indeed, the intensity of the reflected or transmitted reference light beam may be monitored and a drift value indicative of a deviation of the monitored intensity with respect to reference data (a previous measurement or other stored or calibrated data) is thereafter determined. It will be understood that in this case, any deviation of the monitored intensity with respect to a previously monitored intensity is indicative of a variation in time of the monitored reference intensity due to an spurious effects.

The measured light property of the test light beam may be processed using the drift value. Accordingly, the measured intensity of the reflected or transmitted test light beam is corrected using the drift value for example by taking the difference between the measured intensity and the drift value 32 indicative of a variation of the monitored intensity of the reference light beam. It will thus be understood that an artefact in the measured test light beam intensity, which has been caused by an external effect that has also caused in a similar way a variation of the monitored intensity of the reference light beam, can thus be corrected by subtracting the drift value to the measured intensity of the test light beam. The corrected measured intensities of the test light beam can then be further processed, stored or displayed.

Figure 2:
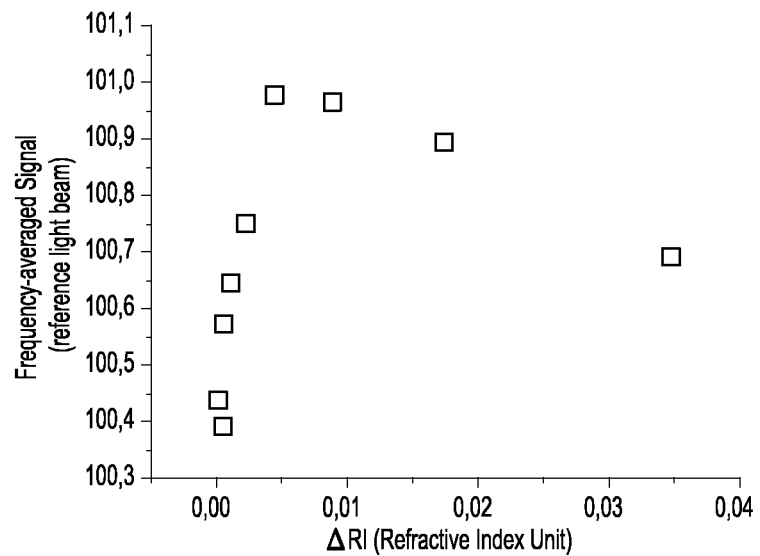
FIG. 2: is a graph showing a set of drift values indicative of variations of monitored intensities of a reference light beam, which have been obtained for different values of refractive index of a medium adjacent to the sensor surface according to the present invention.
Figure 3:
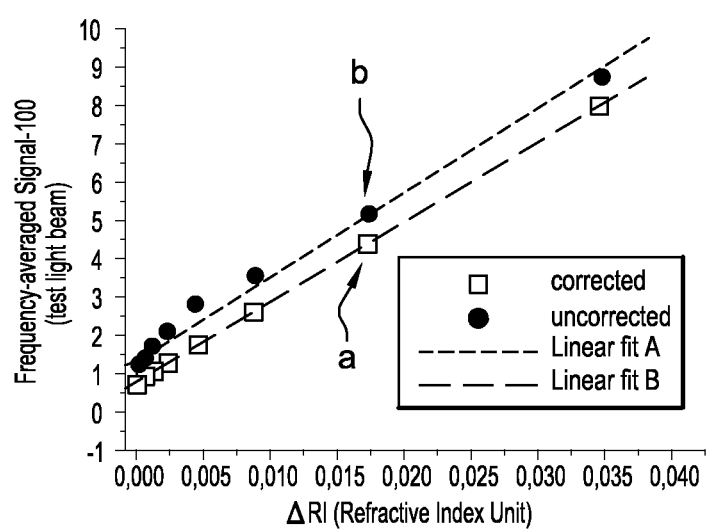
FIG. 3: is a graph presenting sets of corrected and uncorrected frequency-averaged values of measured intensities of a test light beam, which have been obtained for different values of refractive index of a medium adjacent to the sensor surface.

For the sake of exemplification and to better understand the working principle of the present method, let us describe the method with respect to FIGS. 1 to 3, which were obtained using a sensor chip having a sensor surface comprising a periodical gold nanograting. The sensor was investigated in reflection mode by means of a collimated white beam emitted by a tungsten light source at a fixed angle. The reflected light was sensed by means of a CCD spectrum resolved detector (400-1050 µm). As it is known to those skilled in the art, in such setup the nanograting parameters and the angle of incidence determine univocally the optical response of the system and hence the spectral position of the resonances. These resonance peaks result from the shift of the localized and de-localized resonance modes.

The spectra were collected using the following samples: a first sample of pure Phosphate Buffer Solution (PBS, refractive index n=1.334), and then several samples of PBS containing predetermined concentrations of Glycerol (actually from 0.1% up to 25%), providing a known variation of refractive index at the sensor surface. Upon investigating each sample, graph of FIG. 1 was plotted, the vertical axis indicating a so-called Signal calculated as the ratio of the reflected intensity of the samples with varying concentrations of glycerol over the reflected intensity of the pure PBS sample, whereas the horizontal axis shows the wavelength.

For the sample with PBS the signal should ideally be 100%. As can be seen on FIG. 1, in this configuration the Signal is a function of the increasing glycerol concentration, three resonance peaks being observed: a positive peak centred at 760 nm, a negative peak centred at 820 nm and a broad positive peak centred at 900 nm. These peaks result from the localized and de-localized resonance capability of the sensor.

On the right side of the graph the intensities of the peaks (respectively their areas) increase with glycerol concentration. On the left side, the portion of spectrum from 450 nm to 700 nm remains substantially unchanged, but more importantly does not reveal any resonance condition due to the specific configuration that has been selected (properties of the grating, working angle, and wavelength).

So, the variation of refractive index induced by the samples in contact with the sensor surface provides measurable signals that can be observed in the region 750-1050 nm where resonance occurs. On the other hand, in the region 450-700 nm the measured reflected intensities do not vary due to resonance and can be used to monitor fluctuations due to extraneous effects, i.e. artefacts, such as: temperature variations; instabilities of the light source; instabilities of the liquid flow over the sensor surface; shocks; etc.

Hence, a continued or regular monitoring of this non SPR exciting region of the spectrum can be used to detect a punctual or instantaneous variation or a drift of the signal, and can also be used for correcting the measured signal of the reflected light in the resonance range, as will be explained below.

While the spectra shown in FIG. 2 were obtained under white light illumination, as mentioned, one can advantageously simply use two LEDs to perform the same analysis: one to excite the SPR and obtain a significant signal around 900 nm and the other to monitor fluctuations around 525 nm. This possibility is illustrated in FIG. 2 by the rectangles labelled LED1 and LED2 respectively, each LED covering a respective bandwidth of the spectrum. Hence, LED 1 emits the incident test light beam while LED2 emits the incident reference light beam.

Although not used here, LED1' constitutes another possibility for the test light beam. Indeed, a surface plasmon resonance condition can also advantageously be determined by monitoring the difference between a measured "positive" peak (e.g. at 900 nm), which increases as the light-SPR coupling condition changes at the sensor surface, and an observed "negative" peak (e.g. at 820 nm), which increases in the opposite direction than the observed positive peak as the light-SPR coupling condition changes at the sensor surface. Monitoring the differences between these upper lower peaks enable improving the sensitivity of the sensing method. In such case, one may use two LEDs per resonance condition; in the present case, two LEDs for the delocalized resonance and two LEDs for the localized resonance.

It will be noted that the LED1 band and the LED2 band may be separated by an intermediate frequency (MRF), which can correspond to a maximal resonance frequency of SPR at the sensor surface.

Also, when using such monochromatic sources, it is preferred to employ a CCD as detector rather than a spectrometer. The CCD integrates all the light coming from the sample within the bandwidth of the LEDs and typically integrates and averages the signal over time. Another main advantage of using a CCD detector is its spatial resolution so that a map of the surface may be obtained in detecting the locally dependent signal at the sensor surface; multiplexed assays can thus be performed with an appropriately prepared sensor surface.

Turning now to FIG. 2, the plotted values are indicative of the variation of the monitored intensities of the reference light beam, i.e. under illumination with LED2, for the same samples as in FIG. 1. The y-axis here actually indicates the frequency-averaged values of the variation of intensities within the spectral band LED2, which can be calculated as the area of the spectrum within the bandwidth of LED2 divided by the bandwidth. The x-axis indicates the variation of refractive index expressed in refractive index units (RIU). As can be seen, the y-values increase up to refractive index variations of 0.01 RIU and then decreases slightly. Although there was apparently no sensible variation in this bandwidth in FIG. 1, here we can see that fluctuation did occur. This is possibly due to a warming of the system and a subsequent stabilization of the system and makes it clear that it is independent from the change in refractive index on the sensor surface. The variation is consistent up to 1%, and particularly for the lower changes of refractive index where the signal is small.

So, as can be deduced from FIG. 2, the monitoring of the reflected intensity of a control/reference light beam at a wavelength that does not excite SPR permits detecting the occurrence of artefacts. But actually, monitoring the reflected reference light also permits correcting the values obtained under test light illumination and thus improve the quality and sensitivity as well as the limit of detection of the method; this will now be explained with reference to FIG. 3.

FIG. 3 presents two sets of points, one set (a) being corrected for artefacts using the reference signal monitoring and the other set (b) being uncorrected. The points are frequency-averaged test values of the measured intensities of the test light beam that have been obtained by integrating the measured signals over the bandwidth of LED1. However, for the corrected set of points, the corresponding frequency-averaged value obtained by integration of the measured light under reference LED2 is subtracted to the initially obtained frequency-averaged test value. In doing so, the fluctuations due to artefacts are taken into account, and erroneous measurements can be avoided.

As it can be seen, a straight line much better fits the corrected set of points (a) than the uncorrected (b) one. The correction is particularly efficient for the lower variations of the refractive index, where signal to noise is lower.

As it will be clear to those skilled in the art, the corrected linear fit can then advantageously be used as calibration curve to determine the refractive index of a sample.

Figure 4:
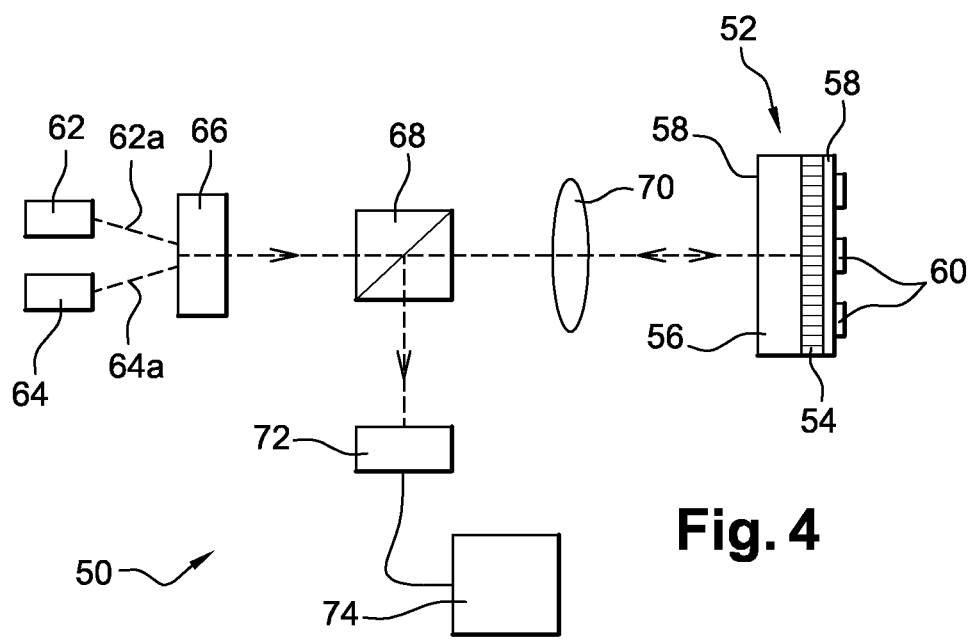
FIG. 4: is a schematic illustration of a preferred SPR sensing system
Figure 5:
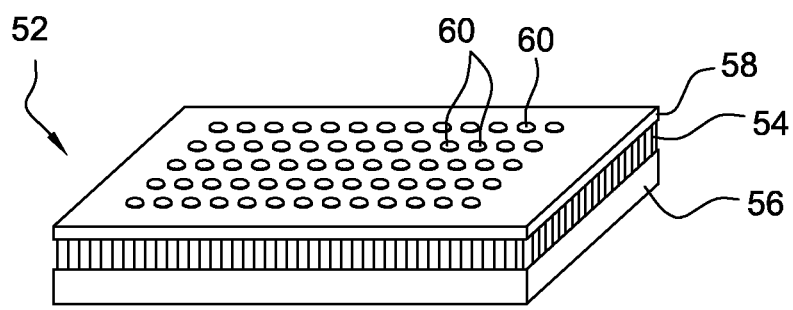
FIG. 5: is a schematic perspective view of a preferred sensor structure for use in biosensing applications.

A preferred embodiment of SPR sensing system 50 adapted for performing the present method is schematically illustrated in FIG. 4. This SPR sensing system 50 is particularly adapted for biosensing applications due to the structure of its sensor 52 that comprises ligands or other targeting moieties attached to the sensing surface 54. Depending on the targeting moieties, the biosensor can be designed to analyse a variety of samples, e.g. measure the concentration of specific chemical or biochemical molecules in a solution such as blood, urine or water etc. The present sensing system 50 is compact and can thus easily be installed and transported for various applications, e.g. to measure medical parameters at a point-of-care, to detect and quantify food and water contamination or to detect explosives, contaminants or toxicants in the atmosphere, etc.

Biosensor 52 has a sensor surface 54 forming the sensing layer and built as a periodic gold nanograting configured to enable generation of SPR, in particular localized and delocalized SPR. As it is known, localized SPR corresponds to surface-bond electromagnetic waves that are confined to defined regions at the sensor surface, whereas delocalized SPR corresponds to surface-bond electromagnetic waves that are not confined to these defined regions at the sensor surface. The sensor surface 54 lies on top of a transparent substrate 56 that is capable of transmitting light so as to allow working in reflection mode from the sensor's backside 58.

Various possible methods of manufacturing such sensor 52 are known in the art. In one embodiment, the transparent substrate 56 comprises a transparent glass or a transparent polymer, for example transparent polystyrene. The sensor surface layer 54 is preferably manufactured by depositing a layer of poly acrylacid (ppAA) over a glass substrate 56 and a subsequent layer of polystyrene beads (PS). The ppAA and PS layers are etched by $O_2$ plasma to form a grating structure comprising regularly spaced pillars of ppAA separated by a sub-micrometric distance. Gold is then deposited over the pillars to fill-in the gaps between neighbouring pillars, and the remainder of the PS mask is removed, obtaining a periodic gold nanograting. Other possible materials for the dielectric pillars are polystyrene or poly-methyl-methacrylate, etc. Instead of a glass substrate, one may use a polymeric substrate, e.g. made from PS or PMMA or other transparent material, that allows direct etching of the substrate to form the pillars.

It will be understood that the geometrical and physical properties of the patterned structure of the sensor surface determine the surface plasmon resonance conditions (resonance coupling) at the sensor surface, in particular the surface plasmon frequencies and a maximum SPR excitation frequency, and thus determine the optical effect of SPR excitation at the sensor surface.

Reference sign 58 indicates a very thin layer of antifouling material, e.g. of antifouling hydrogel, namely poly-ethylene glycol. As it is known, the antifouling material acts in an anti-adhesive manner to prevent or reduce undesired interactions, such as the non-specific absorption of chemical or biochemical molecules etc. at the sensor surface. This reduces noise signals that could have been caused by the interaction or the binding of undesired chemical or biochemical molecules at the sensor surface.

On top of this antifouling layer 58 is a microarray 60 of targeting moieties, i.e. ligand or molecules attached in an organised manner to the antifouling layer that will bind to or immobilize specific biomolecules or other analytes of interest in the liquid sample contacted with the sensor surface. These targeting moieties may comprise antigens/antibiodies, enzymes, proteins, oligonucleotides etc. The target moieties can be easily attached to the antifouling layer by microspotting that allows a wide variety of configurations of the array, varying the size of the spots and the kinds of targeting moieties. Such microspotting technique is e.g. described in the article "*Fabrication and characterization of protein arrays for stem cell patterning*" by Laura Ceriotti et al, published in Soft Matter 2009, 5, 1-12.

Referring now more generally to the optical setup of the SPR system 50, it comprises a test light beam source 62 and a reference light beam source 64. The test light beam source 62 and reference light beam source 64 comprise preferably each a light-emitting diode (LED) or a laser. The test light beam source 62 is configured to emit a test light beam 62*a* having one or more frequencies corresponding to one or more permitted frequencies of SPR at the sensor surface 10 so as to excite resonance. Preferably, the test light beam source 62 is configured to emit a test light beam 62*a* in at least one spectral emission band covering at least one permitted spectral band of SPR at the sensor surface 54, similar to LED1 in FIG. 1.

By contrast, reference light beam source 64 is configured to emit a reference light beam 64*a* of one or more frequencies that do not correspond to permitted frequencies of SPR at the sensor surface 54 so as not to excite SPR. Preferably, the reference light beam source 64 is configured to emit a reference light beam 64*a* in at least one spectral emission band remote from the permitted frequencies of SPR at the sensor surface 54. For example, the reference light beam source 64 may be configured to emit reference light covering a spectral band the spectral limits of which are at a spectral position far at least the double of the Full Width at Half Maximum (FWHM) of the Surface Plasmon Resonance from the Surface Plasmon Resonance peak.

When there is more than one SPR-peak (as e.g. in case there is localized and delocalized peaks), the distance between the resonance peak and reference beam is calculated with respect to the closest SPR-peak. Also, one may consider selecting the reference beam far by at least 2 to 4 times the closest SPR-peak.

It shall be appreciated that in operating at such spectral position for the reference beam it is possible to avoid any excitation of surface plasmonic resonances.

Conventionally in SPR testing the principle is to be able to sense small refractive index changes. And here this means detecting changes relative to the refractive index of the medium containing the biomolecules or other agents to be detected.

But it shall be kept in mind that, as explained above, the spectral position of the surface plasmon resonances (localized and delocalized) is uniquely determined by the structure of the nanograting and the refractive index of the medium containing the biomolecules or other agents to be detected.

When the recognition at the sensor surface occurs, the SPR will shift in the spectrum by a quantity, which is comprised between the limit of detection of the system (minimum detectable spectral shift) and the FWHM of each surface plasmon resonance.

Therefore, selecting a reference beam having a spectral band remote from the SPR and namely having its closest bandwidth-end at least at the double of the FWHM of the SPR peak, avoids exciting the surface plasmons at the SPR-peak otherwise monitored through the test beam.

Referring now more specifically to the present variant having a nanostructured surface SPR sensor surface, one may note that the spectral position of the resonance structure used as a sensitive probe depends on the structural parameters of the nanostructured surface and, in particular, on the size and the shape of the polymeric pillars. As a matter of fact, the resonance corresponds to a charge oscillation mode having the maximum electric field within the surface area of the pillar and near its top. In this instance, this is due to the peculiar cone truncated pillar shape and the corresponding thin circular edge formed by gold on top.

The effect of such a conformation is twofold:
- the electric field is localized and enhanced just on top of the pillar; that is to say, where the probability of attaching the analyte molecules is the highest;
- the conical shape and the refractive index of the substrate allowing this plasmonic mode be easily coupled with plasmonic oscillations of gold on the substrate side, makes such a field enhancement particularly effective when excited from the backside.

At a sufficient spectral distance from this kind of resonance (the double of its FWHM is a good spacing) the high sensitivity related to such a peculiar field configuration is lost because: either the electric field spatial distribution is changed, having its maxima values in different places on both (front or back) surfaces or in the inner of the pillar (where no analyte molecules can be detected); or no matching of the modes through the pillars is allowed, then the excitation of an enhanced field is not transmitted to the sensitive region.

Accordingly, in selecting a reference beam located at twice the FWHM of the SPR peak under monitoring it is possibly to observe optical properties of the sensor surface which are purposively not related to any plasmon resonance supported by the surface.

Although used herein because investigation is made at fixed angle of incidence, one may vary the incidence angle of the reference beam to illuminate the sample under non-SPR motivating conditions.

As can be seen in FIG. 4, the test light beam 62a and the reference light beam 64a are directed towards the sensor surface 54 via an optical setup, which can comprise for example an optical coupler 66, a beam splitter 68 and a lens system 70. The optical coupler 66 is configured to control the alternative or simultaneous transmission of the test light beam 62a and reference light beam 64a towards the sensor surface 54. The lens system 70 is used for transmitting the test and/or reference light beams 62a, 64a to homogenously illuminate the sensor surface 54. It will be noted that the test light beam 62a and/or the reference light beam 64a can illuminate the sensor surface 10 at various angles of incidence, but in the present setup the angle of incidence is fixed. Due to the setup, both the reference and test light beams arrive with the same, fixed angle of incidence on the sensing layer.

As it appears from FIG. 4, the test and reference light beams 62a, 64a are directed towards the sensor surface 54 through the transparent substrate 56, where they reflect on the side of the sensor surface 54 that interfaces with the transparent substrate 56. It will be noted that the light reflected on this internal side of the sensor surface 52 does not interfere with or scatter in the sample lies over the microarray. Internal reflection, i.e. from the backside 58, is thus advantageous in that it avoids any interference of light transmission due to the sample and microarray structure. The light beams reflected on the sensor surface are then directed via the beam splitter 68 to a photosensor 72. The photosensor 72 is adapted to measure the intensity or a quantity indicative thereof, such as the spectral intensities, the absorbance, the reflectance, the reflectivity etc. It will be noted that the photosensor 72 is also adapted to monitor the intensity of the test light beam 62a, in particular of a time- or frequency-averaged value thereof, in one- or two-dimensions, thereby enabling e.g. simultaneous detection of many local changes in the light-SPR coupling condition at the sensor surface 54. Advantageously, the photosensor 72 can be adapted to provide a one- or two-dimensional image of a measured or monitored intensity. It will be understood that such one- or two-dimensional operating of the photosensor 72 enables e.g. the simultaneous detection of many different molecules of interest that interact at or bind to the sensor surface 54. Such a one- or two-dimensional SPR imaging photosensor 72 enables the high-throughput analysis of chemical or biochemical events at the sensor surface 54 and also permits reducing the average cost-per-assay of the sensing system.

In a preferred embodiment, the photosensor 72 preferably comprises a time- and/or spectrum—resolved camera based on a charge-coupled device (CCD) or on a photodiode array for measuring the intensity of the test light beam 62a and for detecting intensity changes of the reflected reference light beam 64a. Preferably, this camera is adapted to resolve a measured signal over short time intervals, which are typically in the millisecond range. More preferably, this camera can also output signals indicative of successive measurements of time- and/or frequency-averaged intensities of the test light beam 62a and/or of the reference light beam 64a. The camera can also be adapted to measure the spectral intensities of the reflected test light beam 62a and to output a signal indicative of a measured average spectral intensity, i.e. indicative of a mean value of measured spectral intensities, or any signal indicative thereof.

The signals corresponding to the monitored intensities of the reference light beams and the signals corresponding to the measured intensities of the test light beam are then transmitted to a processor 74. Advantageously, the processor 74 enables detecting an occurrence of SPR excitation by detecting a graded reduction in the measured reflected intensity of test light, and in particular by detecting a dip in the spectrum of the measured intensity of the reflected test light beam 62a caused by the absorption of light at the sensor surface 542. It will be understood that a measured intensity of the test light beam 62a can also be indicative of a measured time- or frequency-weighted average intensity of the test light beam or of a change thereof.

Moreover, the photosensor 72 is adapted to detect a change in the monitored reflected intensity of the reference light beam 64a, in particular a change in a monitored time- or frequency-weighted average intensity, a change in monitored a spectral intensity, a change in the monitored absorbance, a change in the monitored reflectance or reflectivity etc., of the reference light beam 64a as reflected by the sensor surface 52 so as to determine the occurrence of an artefact.

The processor 74 is configured to process, in particular to filter the measurements of the photosensor 72. This processor 74 is preferably programmed to correct the measured intensities of the test light beam 62a in the manner described herein before and to estimate a change in the refractive index at the sensor surface in the above described manner.

The invention claimed is:

1. A SPR sensing method comprising the steps of:
providing a SPR sensor comprising a SPR supporting sensor surface;
contacting a sample to be analysed with said sensor surface and monitoring at least one resonance condition at said SPR supporting sensor surface by illuminating said sensor surface with an SPR exciting test light beam and sensing the reflected or transmitted test light beam;
determining at least one property of said reflected or transmitted test light beam;
illuminating said sensor surface with a reference light beam under conditions selected so as not to excite SPR at said sensor surface and sensing the intensity of the reflected or transmitted reference light beam;
wherein the determination of said at least one property of said reflected or transmitted test light beam takes into account the sensed intensity of the reflected or transmitted reference light beam.

2. The method according to claim 1, wherein said at least one property of said reflected or transmitted test light beam is filtered or corrected based on said sensed intensity of the reflected or transmitted reference light beam.

3. The method according to claim 1, wherein a drift value indicative of a deviation of said sensed intensity of said reference light beam with respect to reference data is determined, and said drift value is used in the determination of said at least one property of said reflected or transmitted test light beam.

4. The method according to claim 3, wherein said reference data is indicative of a previously monitored intensity of said at least one reference light beam and said drift value is indicative of a deviation of said monitored intensity with respect to said previously monitored intensity.

5. The method according to claim 3, wherein said drift value is used for concluding to the occurrence of an artefact of said measured light property and wherein said measured light property is examined for correctness or for incorrectness based on the occurrence of an artefact.

6. The method according to claim 1, wherein the measured light property of at least one test light beam is a measured intensity, in particular a measured time- or frequency-weighted average intensity, or a change in a measured intensity, in particular a change in a measured time- or frequency-weighted average intensity, of the at least one test light beam.

7. The method according to claim 3, wherein using said drift value to correct a measured intensity, in particular a measured time- or frequency-weighted average intensity, or a change in a measured intensity, in particular a change in a measured time- or frequency-weighted average intensity, of the at least one reflected or transmitted test light beam.

8. The method according to claim 7, wherein said drift value is indicative of an amplitude of variation of said reference reflected or transmitted reference light beam and said at least one property of said reflected or transmitted test light beam is an intensity value obtained by substrating said drift value to the measured intensity value of said reflected or transmitted test light beam.

9. The method according to claim 1, wherein said sensor surface comprises a periodic nanograting of a noble metal.

10. The method according to claim 1, wherein targeting moieties are attached on said sensor surface, which exhibit binding specificity to desired analytes, said targeting moieties being preferably organised as a microarray.

11. The method according to claim 1, wherein said test light beam and said reference light beam are each produced by a respective monochromatic light source.

12. The method according to claim 1, wherein each resonance condition is monitored using at least two test light beam of centred on respective, SPR motivating spectral positions.

13. The method according to claim 1, wherein said reference light beam emits reference light covering a spectral band, the spectral limits of which are at a spectral position far at least the double of the Full Width at Half Maximum of the Surface Plasmon Resonance from the Surface Plasmon Resonance peak.

14. A SPR sensing system comprising:
a SPR sensor comprising a SPR supporting sensor surface;
at least one test light source emitting at least one test light beam for illuminating the sensor surface under conditions selected so as to excite SPR at the sensor surface,
a photosensor to measure a light property of said at least one test light beam as transmitted or as reflected by the sensor surface so as to monitor a condition of resonance at the sensor surface,
at least one reference light source emitting at least one reference light beam for illuminating the sample under conditions selected so as not to excite surface plasmon resonance at said sensor surface, wherein said photosensor is also adapted to monitor an intensity of at least one reference light beam as transmitted or as reflected by said sensor surface; and
processor means configured to determine a least one property of said reflected or transmitted test light beam taking into account the sensed intensity of the reflected or transmitted reference light beam.

15. The SPR sensing system according to claim 14, wherein said reference light beam emits reference light covering a spectral band the spectral limits of which are at a spectral position far at least the double of the Full Width at Half Maximum of the Surface Plasmon Resonance from the Surface Plasmon Resonance peak.

16. The SPR sensing system according to claim 14, wherein the photosensor is adapted to measure an intensity, in particular a time- or frequency-weighted average intensity, or a change in intensity, in particular a change in a time- or frequency-weighted average intensity, of at least one test light beam as transmitted or as reflected by the sensor surface.

17. The SPR sensing system according to claim 14, wherein the photosensor is adapted to monitor an intensity, preferably a time- or frequency-weighted average intensity of the at least one reference light beam as reflected or as transmitted by the sensor surface, and said processor is configured to use a drift value to correct the measured intensity, the measured time- or frequency-weighted average intensity or a change thereof.

18. The SPR sensing system according to claim 14, wherein the processor means is operationally connected to storage means for storing or reading calibration data, where the processor means is adapted to estimate a change in the refractive index at the sensor surface by comparing the calibration data with a change in a measured intensity, in particular with a change in a measured time- or frequency-weighted average intensity, of the at least one test light beam.

19. The SPR sensing system according to claim 14, wherein the at least one test light beam source is a monochromatic light source emitting at one or more frequencies that match with one or more frequencies of SPR at the sensor surface so as to excite SPR; and the at least one reference light beam source is a monochromatic light source configured to emit at one or more frequencies that do not match with one or more frequencies of SPR at the sensor surface so as to not excite SPR.

* * * * *